US008448506B2

(12) United States Patent
Yoon et al.

(10) Patent No.: US 8,448,506 B2
(45) Date of Patent: May 28, 2013

(54) ADHESION TEST METHOD USING ELASTIC PLATE

(75) Inventors: Yeo-Hoon Yoon, Hwaseong-si (KR); Ho-Jeong Moon, Cheonan-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 611 days.

(21) Appl. No.: 12/704,960

(22) Filed: Feb. 12, 2010

(65) Prior Publication Data

US 2010/0206062 A1 Aug. 19, 2010

(30) Foreign Application Priority Data

Feb. 13, 2009 (KR) ........................ 10-2009-0012064

(51) Int. Cl.
*G01N 19/04* (2006.01)
(52) U.S. Cl.
USPC ................ 73/150 A; 73/760; 73/788; 73/849; 73/856
(58) Field of Classification Search
USPC ............... 73/150 A, 760, 788, 849, 852, 856, 73/783, 799; 257/48
See application file for complete search history.

(56) References Cited

U.S. PATENT DOCUMENTS 5,768,936 A * 6/1998 Mann ........................ 73/150 A
6,936,843 B2 * 8/2005 Cui .................................. 257/48

FOREIGN PATENT DOCUMENTS

JP 6-13276 A 1/1994
KR 10-1998-0016865 A 6/1998

OTHER PUBLICATIONS

Author: R.H. Dauskardta, M. Lanea, Q. Mab, N. Krishna, Title: "Adhesion and debonding of multi-layer thin film structures", Date: 1998, Publisher: Engineering Fracture Mechanics, vol. 61, pp. 141-162.*
Authors: Ines Hofinger, Matthias Oechsner, Hans-Achim Bahr and Michael V. Swain, Title: "Modified four-point bending specimen for determining the interface fracture energy for thin, brittle layers", Publication: International Journal of Fracture 92: pp. 213-220, Date: 1998. © 1998 Kluwer Academic Publishers.*
Authors: Y. Yamazaki, A. Schmid and A. Scholz, Title: "The determination of the delamination resistance in thermal barrier coating system by four-point bending tests", Date: Feb. 7, 2006, Publisher: Elsevier B.V., Publication: ScienceDirect, Surface & Coatings Technology 201 (2006), pp. 744-754.*

* cited by examiner

*Primary Examiner* — Lisa Caputo
*Assistant Examiner* — Roger Hernandez-Prewitt
(74) *Attorney, Agent, or Firm* — Sughrue Mion, PLLC

(57) ABSTRACT

Provided is a method for testing adhesion. The method includes forming thin films on a substrate; attaching an elastic plate to the substrate, wherein the elastic plate has a larger elastic coefficient than the substrate; and performing an adhesion test on the thin films using an adhesion test apparatus.

17 Claims, 10 Drawing Sheets

ADHESION TEST METHOD USING ELASTIC PLATE

PRIORITY STATEMENT

This application claims priority under 35 U.S.C. §119 from Korean Patent Application No. 10-2009-0012064, filed on Feb. 13, 2009, the contents of which are hereby incorporated herein by reference in its entirety.

BACKGROUND

1. Field

Exemplary embodiments relate to an adhesion test method using an elastic plate, and more specifically, to an adhesion test method which can stably measure adhesion between thin films.

2. Description of Related Art

Semiconductor devices include thin films composed of various materials stacked therein. Recently, to improve the driving capability of semiconductor devices, high-k and low-k insulating layers, metal layers and diffusion barriers composed of new materials are being developed.

In order for semiconductor devices to be reliably driven, stable adhesion between thin films is essential. Accordingly, there is a demand for a test method which accurately and stably calculates adhesion between the thin films, that is, peel energy, composed of various materials.

SUMMARY

Exemplary embodiments provide an adhesion test method which can accurately and stably measure adhesion between the same kind or different kinds of thin films without damaging an adhesion test sample.

According to an aspect of the exemplary embodiments, provided is a method of testing adhesion, the method including: forming thin films on a substrate; attaching an elastic plate to the substrate, wherein the elastic plate has a larger elastic coefficient than the substrate; and performing an adhesion test on the thin films using an adhesion test apparatus.

The thin films may be formed on one surface of the substrate, and the elastic plate may be attached to the one surface of the substrate through an adhesive member.

After forming the thin films, a notch may be formed across the other surface in the other surface opposite to the one surface of the substrate.

At least one thin film, which is to be peeled off among the thin films, may be formed such that one end thereof is disposed at a position vertically corresponding to the notch.

The thin films may be formed of any one of an insulating layer, a metal layer, an adhesive agent, and an adhesive film.

A four point bending test apparatus may be used as the adhesion test apparatus.

The adhesion test may include applying pressures to the substrate and the elastic plate to peel the thin films from each other, and measuring energy when the thin films are peeled off.

The pressure applied to the substrate may be applied to both edges of the substrate toward the elastic plate, and the pressure applied to the elastic plate may be applied to portions corresponding to positions between the pressure-applied portions of the substrate toward the substrate.

The substrate may be formed of a semiconductor wafer, and the elastic plate may be formed of a metal including spring steel or a high molecular material.

After attaching the substrate to the elastic plate, the warpage of the elastic plate and the substrate attached to each other may be measured.

BRIEF DESCRIPTION OF THE DRAWINGS

The above and/or other aspects will become apparent and more readily appreciated from the exemplary embodiments, as described in further detail below with reference to the accompanying drawings. It should be understood that various aspects of the drawings may have been exaggerated for clarity.

DETAILED DESCRIPTION OF EXEMPLARY EMBODIMENTS

Figure 1:
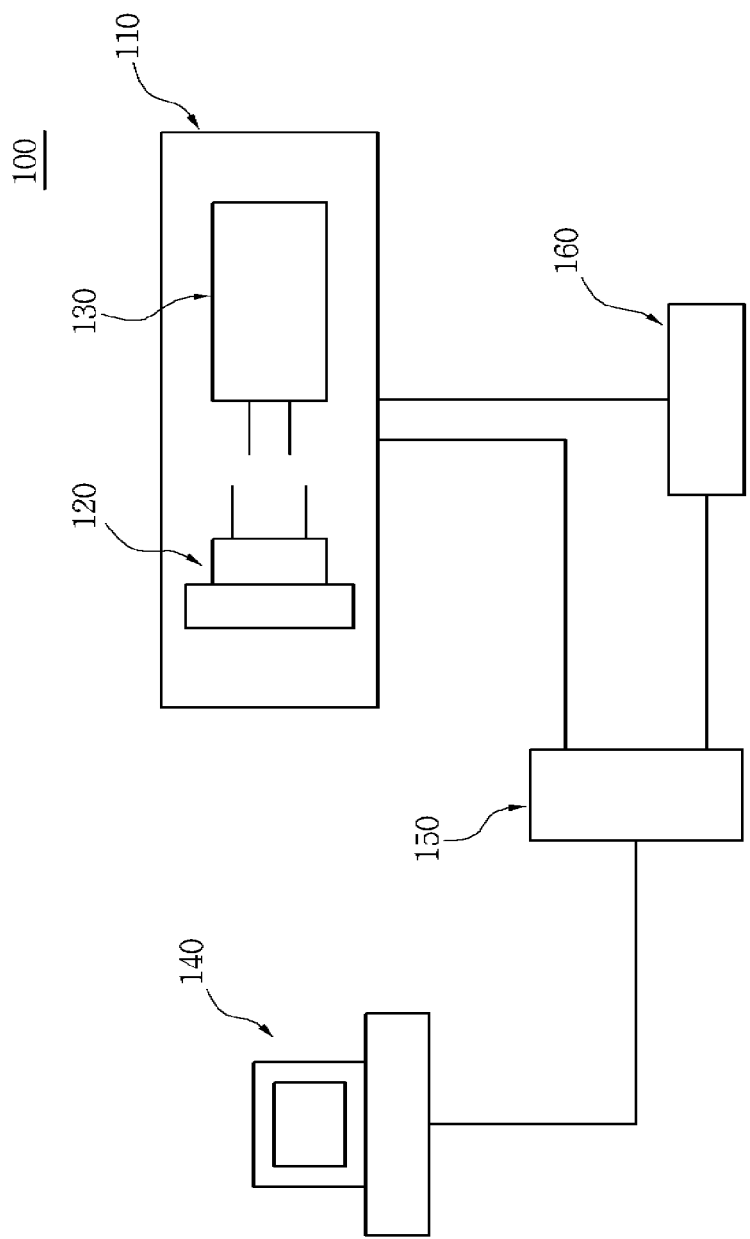
FIG. 1 is a diagram of an adhesion test apparatus according to an exemplary embodiment.

Various exemplary embodiments will now be described more fully with reference to the accompanying drawings in which some exemplary embodiments are shown. In the drawings, the thicknesses of layers and regions may be exaggerated for clarity.

Detailed exemplary embodiments are illustrated herein. However, specific structural and functional details disclosed herein are merely representative for purposes of describing the exemplary embodiments. The inventive concept herein, however, may be embodied in many alternate forms and should not be construed as limited to only the exemplary embodiments set forth herein.

Accordingly, while exemplary embodiments are capable of various modifications and alternative forms, exemplary embodiments thereof are shown in the drawings and will herein be described in detail. It should be understood, however, that there is no intent to limit the exemplary embodiments to the particular forms disclosed, but on the contrary, the exemplary embodiments are to cover all modifications, equivalents, and alternatives falling within the scope of the inventive concept. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of exemplary embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of exemplary embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof. Spatially relative terms, such as "beneath," "below," "lower," "above," "upper" and the like, may be used herein for ease of description to describe one element or a relationship between a feature and another element or feature as illustrated in the figures. It will be understood that the spatially relative terms are intended to encompass different orientations of the device in use or operation in addition to the orientation depicted in the Figures. For example, if the device in the figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

Exemplary embodiments are described herein with reference to cross-sectional illustrations that are schematic illustrations of idealized exemplary embodiments (and intermediate structures). As such, variations from the shapes of the illustrations as a result, for example, of manufacturing techniques and/or tolerances, may be expected. Thus, exemplary embodiments should not be construed as limited to the particular shapes of regions illustrated herein but may include deviations in shapes that result, for example, from manufacturing. Therefore, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative exemplary embodiments, the functions/acts noted may occur out of the order noted in the figures. For example, two figures shown in succession may in fact be executed substantially concurrently or may sometimes be executed in the reverse order, depending upon the functionality/acts involved.

In order to more specifically describe exemplary embodiments, various aspects will be described in detail with reference to the attached drawings. However, the inventive concept is not limited to exemplary embodiments described.

Recent developments in semiconductor packages have shown a tendency toward lighter, thinner, shorter, and smaller designs with higher capacity. Accordingly, the line width of circuit interconnections of semiconductor devices composing a semiconductor package is being reduced. Further, the development of a method for forming interconnections using low-resistance materials is being accelerated. In addition, high-k and low-k insulating layers, metal layers, and diffusion barriers composed of new materials are being developed to stably drive semiconductor devices and improve the driving capability thereof.

Meanwhile, semiconductor devices include the same kind or different kinds of thin films stacked therein, the thin films being formed of various materials. To reliably drive a semiconductor device, stable adhesion between thin films composing the semiconductor device is essential. Defective adhesion between the thin films may cause various problems not only in the reliability aspect of the semiconductor device, but also in the reliability aspect of a semiconductor package. That is, insulating layers attached to each other and an insulating layer and metal patterns attached to each other in the semiconductor device, respectively, may be peeled off of each other in a manufacturing process of the semiconductor device including a process of forming metal wires, a process of sawing a wafer, and a process of cutting a fuse unit. For example, a SiOCH film used as an interlayer insulating layer of a semiconductor device and a SiN or SiCN film disposed as an insulating layer on and under the SiOCH film may be peeled off of each other. Further, the SiN film as an insulating layer and interconnection patterns formed of Cu and disposed on the SiN film may be peeled off of each other.

Accordingly, to form a reliable semiconductor device, a test method for accurately and stably calculating adhesion between thin films, that is, peel energy, needs to be developed.

Hereinafter, an adhesion test apparatus and an adhesion test method using the same according to exemplary embodiments will be described in detail.

Figure 2:
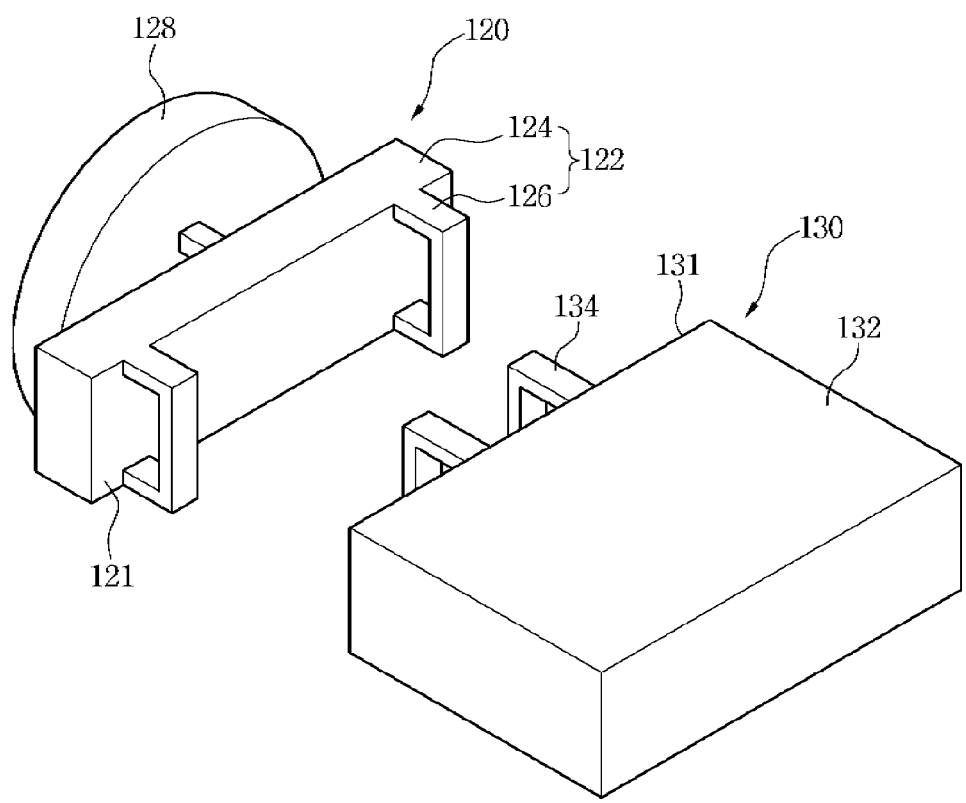
FIG. 2 is a perspective view of a testing unit of the adhesion test apparatus according to an exemplary embodiment.

FIG. 1 is a diagram of an adhesion test apparatus according to exemplary embodiments. FIG. 2 is a perspective view of a testing unit of the adhesion test apparatus according to exemplary embodiments.

Referring to FIG. 1, the adhesion test apparatus 100 according to exemplary embodiments may include a testing unit 110, a computer 140, a controller 150, and a power supply 160. The adhesion test apparatus 100 may be a four-point bending test apparatus.

The testing unit 110 may test peel energy between stacked thin films, i.e., the measured adhesion between the thin films. The testing unit 110 may peel the thin films from each other using mechanical power. The thin films are formed in an adhesion test sample.

The computer 140 may be connected to the controller 150, and may execute and control an adhesion test, which may be performed by the testing unit 110, through the controller 150. The computer 140 may store pressure data applied from the testing unit 110 when the thin films are peeled off. The computer 140 may convert the pressure data into peel energy through software for analysis in various forms.

The controller 150 may execute a test command applied from the computer 140 to drive the testing unit 110. The controller 150 may deliver the pressure data obtained from the testing unit 110 to the computer 140.

The power supply 160 may supply proper power to drive the controller 150 and the testing unit 110.

Referring to FIGS. 1 and 2, the testing unit 110 may include a fixed part 120 and an actuator 130.

The fixed part 120 may include a load cell 128 and a bending jig 122. The bending jig 122 may include a jig body 124 and a pair of first supporters 126.

The load cell 128 may be connected to the bending jig 122, and may be a pressure sensor which measures pressures acting on the bending jig 122. The pressure data measured by the load cell 128 may be stored in and displayed on the computer 140 through the controller 150.

The bending jig 122 may be a member where test samples having thin films formed thereon are disposed. The pair of first supporters 126 may be disposed on one surface 121 of the jig body 124 to be spaced from each other. The first supporters 126 may have various shapes such that the test samples are easily and stably disposed. That is, each of the first supporters 126 may be formed in such a C shape as to form a closed loop with the one surface 121 of the jig body 124. Alternatively, although not shown, the first supporters 126 may have an L shape.

The actuator 130 may have an actuator body 132 and a pair of second supporters 134. The actuator 130 may be disposed to face the bending jig 122 of the fixed part 120. That is, the second supporters 134 may be disposed to face the first supporters 126. The second supporters 134 may be disposed between the first supporters 126 provided on the fixed part 120. Accordingly, the second supporters 134 may be spaced at a smaller distance from each other than the first supporters 126.

The second supporters 134 may form a symmetrical shape with the first supporters 126. According to an embodiment of the invention, each of the second supporters 134 may be formed in such a C shape as to form a closed loop with one surface 131 of the actuator body 132. According to the other exemplary embodiments of the invention, although not shown, the second supporters 134 may have various shapes including an L shape.

The actuator 130 may horizontally move toward or away from the fixed part 120 in response to a driving command from the computer 140 and the controller 150. The actuator 130 may move a constant distance per predetermined time in response to a command signal from the computer 140 and the controller 150.

FIGS. 3 to 12 are diagrams for explaining an adhesion test method according to exemplary embodiments. FIG. 13 is a diagram for explaining peel energy between thin films.

FIGS. 3 to 12 include the same components as the adhesion test apparatus illustrated and described in FIGS. 1 and 2. Therefore, duplicated descriptions of the same components will be omitted, and like names and reference numerals will be used for the same components.

Figure 3:
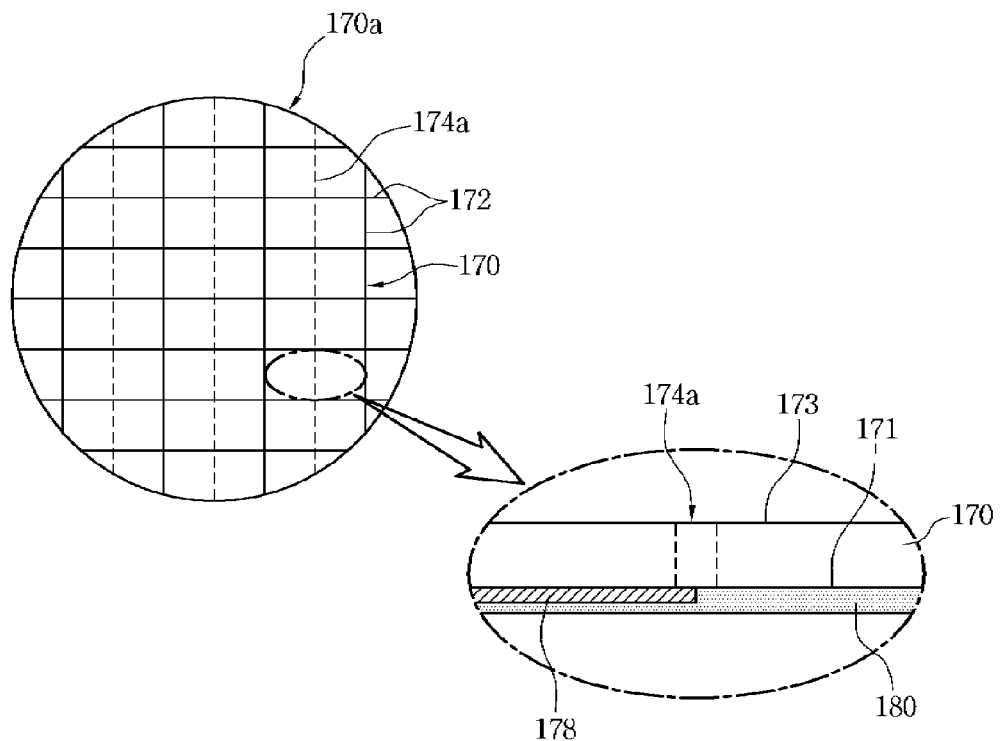
FIGS. 3 to 12 are diagrams for explaining an adhesion test method according to exemplary embodiments.

Referring to FIG. 3, a wafer 170a having a plurality of substrates 170 partitioned by scribe lines 172 may be provided. The wafer 170a may have an upper surface 171 and a lower surface 173 facing the upper surface 171. The wafer 170a may be a semiconductor wafer. The wafer 170a may have a notch formation region 174a disposed on the lower surface 173 of each of the substrates 170.

A plurality of thin films may be formed on the upper surface 171 of the substrate 170. The thin films may include first and second thin films 178 and 180 which are to be peeled off. The first thin film 178 may be a measurement target film for measuring adhesion with respect to the second thin film 180. The first thin film 178 may be formed such that one end thereof is disposed at a portion which vertically corresponds to the notch formation region 174a. The second thin film 180 does not need to be formed in the same shape as the first thin film 178. Preferably, the second thin film 180 may be formed to cover the first thin film 178 for the sake of a stable test.

According to other exemplary embodiments of the invention, a plurality of buffer layers (not shown) may be formed between the upper surface 171 of the substrate 170 and the first and second thin films 178 and 180, in order to stably form the first and second thin films 178 and 180. That is, the buffer layers may be formed between the first or second thin film 178 or 180 and the upper surface of the substrate 170, in order to prevent defective interface adhesion. The adhesion between the substrate 170 and the buffer layers may be stronger than that between the first and second thin films 178 and 180.

The first and second thin films 178 and 180, which are to be peeled off, may respectively be formed of the same kind or different kinds of materials. The first and second thin films 178 and 180 may be formed of any one of an insulating layer, a metal layer, an adhesive agent, and an adhesive film. An insulating layer may be an insulating material used for manufacturing semiconductor devices, including SiN, SiOCH, TEOS, SiCN, low-k dielectric, high-k dielectric, etc. Further, a metal layer may be a metallic material used for manufacturing semiconductor devices, including Cu, Au, etc. An adhesive agent or the adhesive film may be an adhesive material for manufacturing semiconductor devices.

Figure 4:
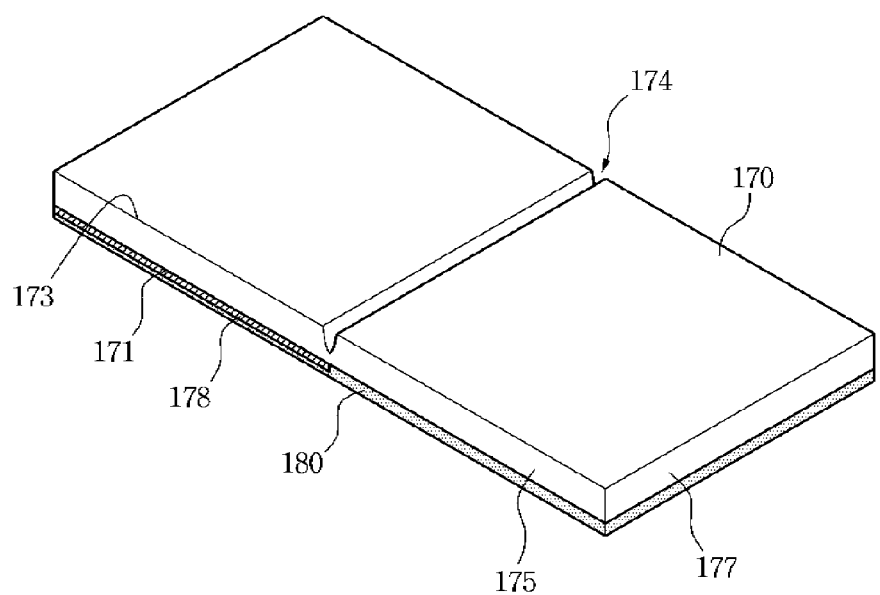

Referring to FIG. 4, a blade may be used to form a notch 174 having a predetermined depth in the notch formation region provided on the lower surface 173 of the substrate 170.

The wafer may be cut along the scribe lines by a blade to be divided into the plurality of substrates 170 having the notch 174 formed therein.

When seen from the plan view, the substrate 170 may have a rectangular shape having first surfaces 175 and second surfaces 177 perpendicular to the first surfaces 175. The first surfaces 175 may be major axis surfaces having a larger length than the second surfaces 177, in consideration of an adhesion test which is to be performed with pressures applied thereto.

The first and second surfaces 175 and 177 of the substrate 170 may have a length of several to several tens of millimeters. The first and second surfaces 175 and 177 of the substrate 170 may have lengths of about 60 mm and 6 mm, respectively. The substrate 170 may have a thickness of several hundreds of micrometers, and more particularly, a thickness of about 800 µm. The length and thickness of the substrate may differ depending on the environment of the adhesion test.

The notch 174 formed on the lower surface 173 of the substrate 170 may be formed between the pair of first surfaces 175. That is, the notch 174 may be formed parallel to the second surfaces 177 of the substrate 170. The notch 174 may be formed across the lower surface of the substrate 170. Only one notch 174 may be formed on the lower surface of the substrate 170. The notch 174 may be formed to be disposed in the center of the first surfaces 175. Specifically, pressure which is to be applied to the substrate 170 during the adhesion test may be applied to both edges of the lower surface 173 parallel to the second surfaces 177. Therefore, the notch 174 may be formed in the center between the edges to which the pressure is applied. Accordingly, the notch 174 may damage the substrate 170 due to a small pressure such that the first thin film 178 is easily peeled from the second thin film 180, during the adhesion test.

The notch 174 may be formed to various depths. For example, the notch 174 may have a depth corresponding to about ⅔ of the thickness of the substrate 170.

Figure 5:
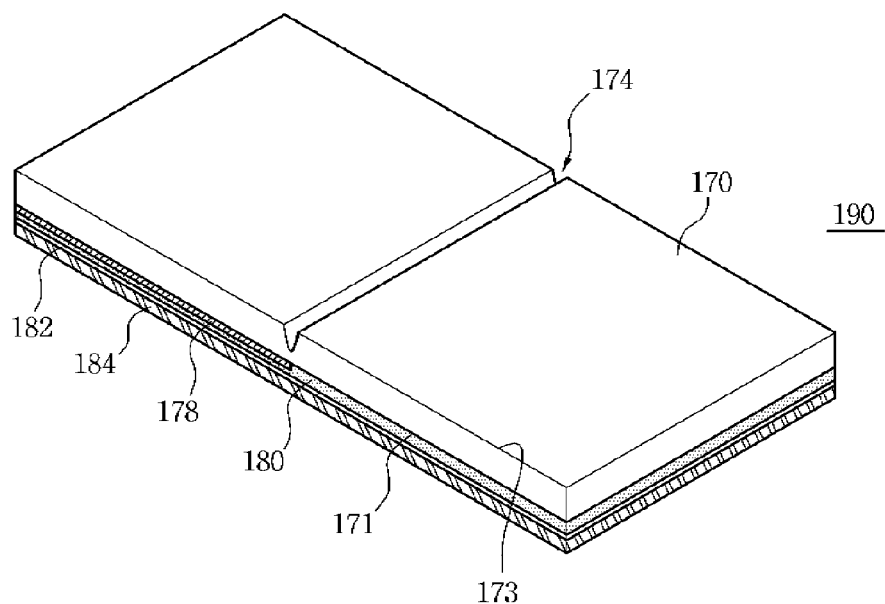

Referring to FIG. 5, an elastic plate 184 may be attached on the upper surface 171 of the substrate 170 through an adhesive member 182. The adhesive member 182 may be formed of epoxy, for example.

The adhesive member 182 may be cured through a thermal process to form an adhesion test sample 190 including the substrate 170 and the elastic plate 184. The thermal process may be performed inside a curing chamber at a temperature of about 100° C. for two hours.

The elastic plate 184 may have the same surface area as the substrate 170. The elastic plate 184 may have a larger elastic coefficient than the substrate 170. The elastic plate 184 may be formed of a material having such an elastic coefficient that it is warped but is not damaged by external pressure. The elastic plate 184 may be formed of metals including spring steel and alloys or a high molecular substance having elasticity. According to an exemplary embodiment, the elastic plate 184 may be formed of SK-5 spring steel having a hardness of 190 HV and a carbon content of 0.8-109%. Alternatively, the elastic plate 184 may be formed of stainless steel having a modulus of about 170 GPa.

The elastic plate 184 may have various thicknesses in consideration of properties of a material to be formed.

According to an exemplary embodiment of the invention, buffer layers for facilitating adhesion may be disposed between the first and second thin films 178 and 180 or between the second thin film 180 and the adhesive member 182. The adhesion between the buffer layer and the adhesive member 182, between the buffer layers and the first and second thin films 178 and 180, or between the buffer layers and the second thin films 180 may be stronger than that between the first and second thin films 178 and 180.

Figure 6:
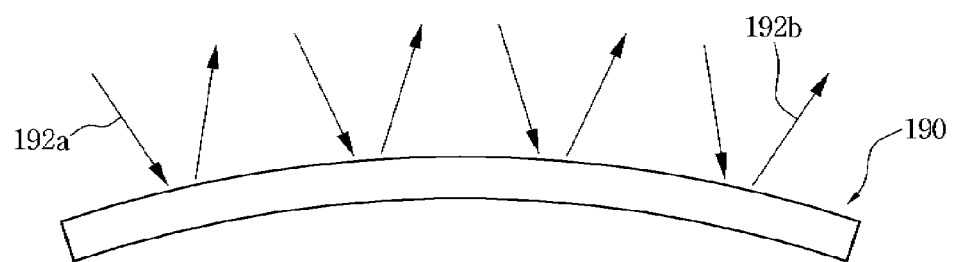

Referring to FIG. 6, it is possible to measure the warpage of the test sample 190. The warpage may occur as the elastic plate 184 and the substrate 170 having different properties, i.e., different thermal expansion coefficients, are attached to each other. The measurement of the warpage may be performed to calculate residual stress of the test sample 190 caused by the warpage. In other words, this may be performed to accurately calculate the adhesion between the first and second films, that is, peel energy, in consideration of the residual stress of the test sample 190 caused by the warpage in the process of testing the adhesion between the thin films.

The warpage measurement for the test sample 190 may be performed using the curvature of the test sample 190. Further, the warpage of the test sample 190 may be measured through various methods. Under one method, the warpage of the test sample 190 may be measured by a shadow moiré system. The shadow moiré system may be an apparatus which measures the curvature of the test sample 190 using light 192a irradiated onto the test sample 190 and light 192b reflected therefrom. The warpage measurement method using the shadow moiré system is a well-known method, and thus the detailed descriptions thereof will be omitted.

Figure 7:
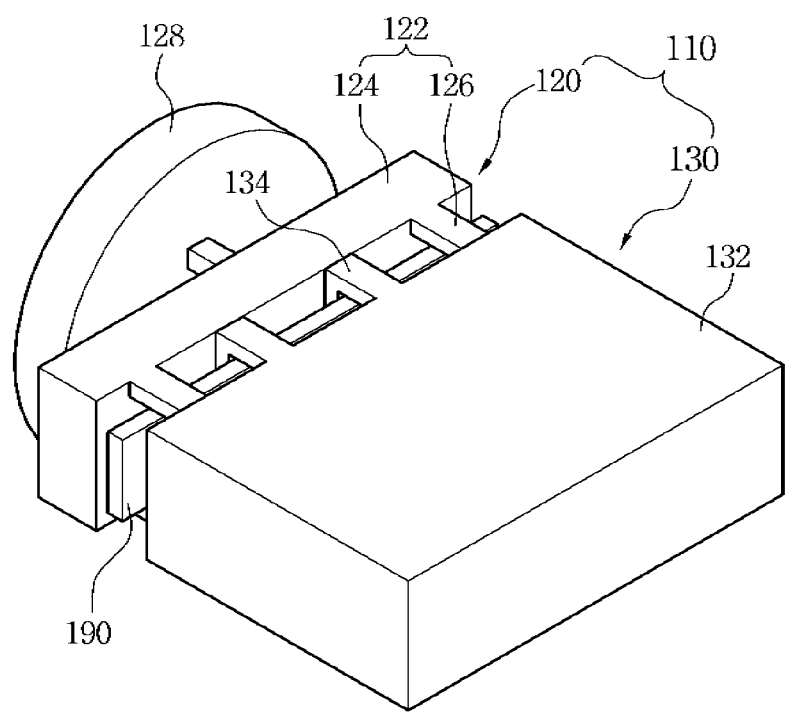
Figure 8:
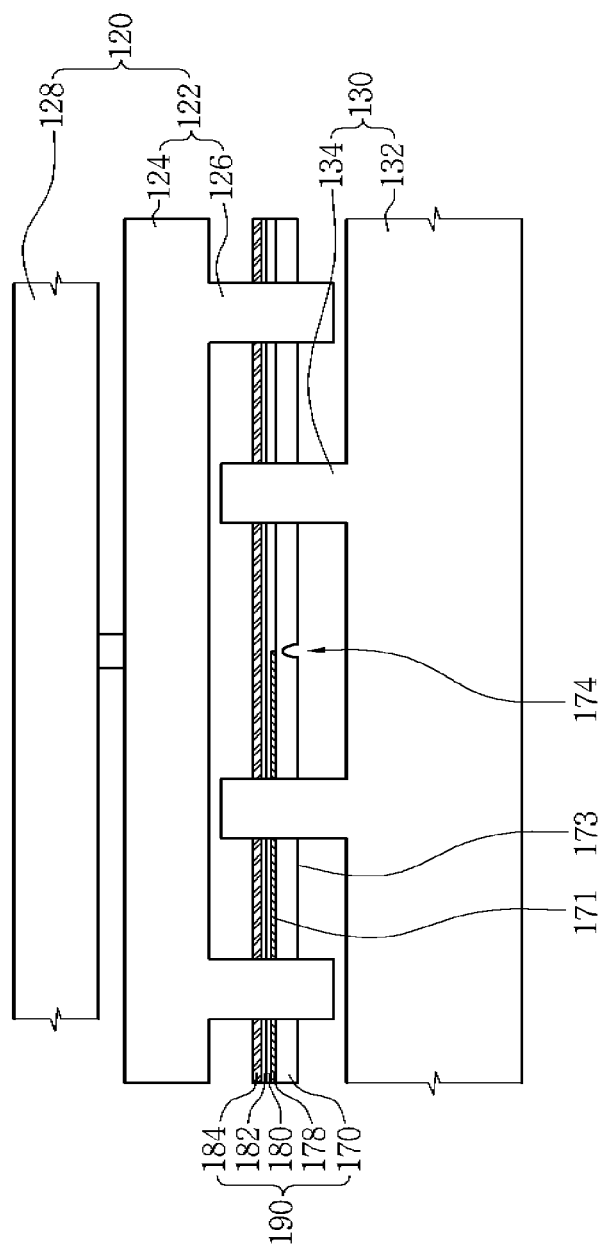

Referring to FIGS. 7 and 8, the test sample 190 may be disposed in the testing unit 110 of the adhesion test apparatus.

Specifically, the actuator 130 may be moved toward the fixed part 120 such that the second supporters 134 provided in the actuator 130 are disposed between the first supporters 126 of the bending jig 122 provided in the fixed part 120.

The test sample 190 may be disposed between the first and second supporters 126 and 134. At this time, the test sample 190 may be disposed such that the upper and lower surfaces 171 and 173 of the substrate 170 face the fixed part 120 and the actuator 130, respectively. The first supporters 126 may be disposed to support both edges of the lower surface 173 of the substrate 170 composing the test sample 190. The second supporters 134 may be disposed adjacent to the central portion of the test sample 190 outside the notch 174 of the test sample 190. The second supporters 134 may be disposed to support the elastic plate 184 of the test sample 190.

Figure 9:
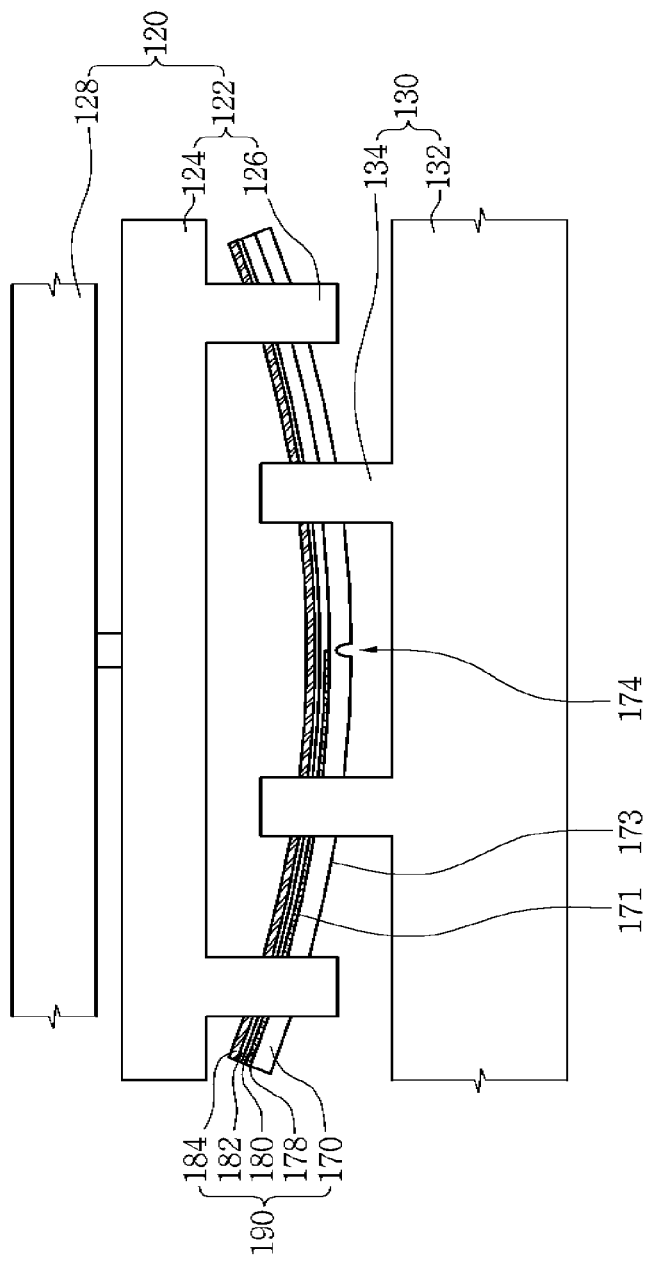

Referring to FIG. 9, the actuator 130 may be moved in a direction away from the fixed part 120 such that the central portion of the test sample 190 is warped toward the actuator 130. The actuator 130 can move a constant distance per predetermined time.

Through the movement of the actuator 130, pressure may be continuously applied to the central portion of the test sample 190 by the first supporters 126 of the fixed part 120 and the second supporters 134 of the actuator 130.

Figure 10:
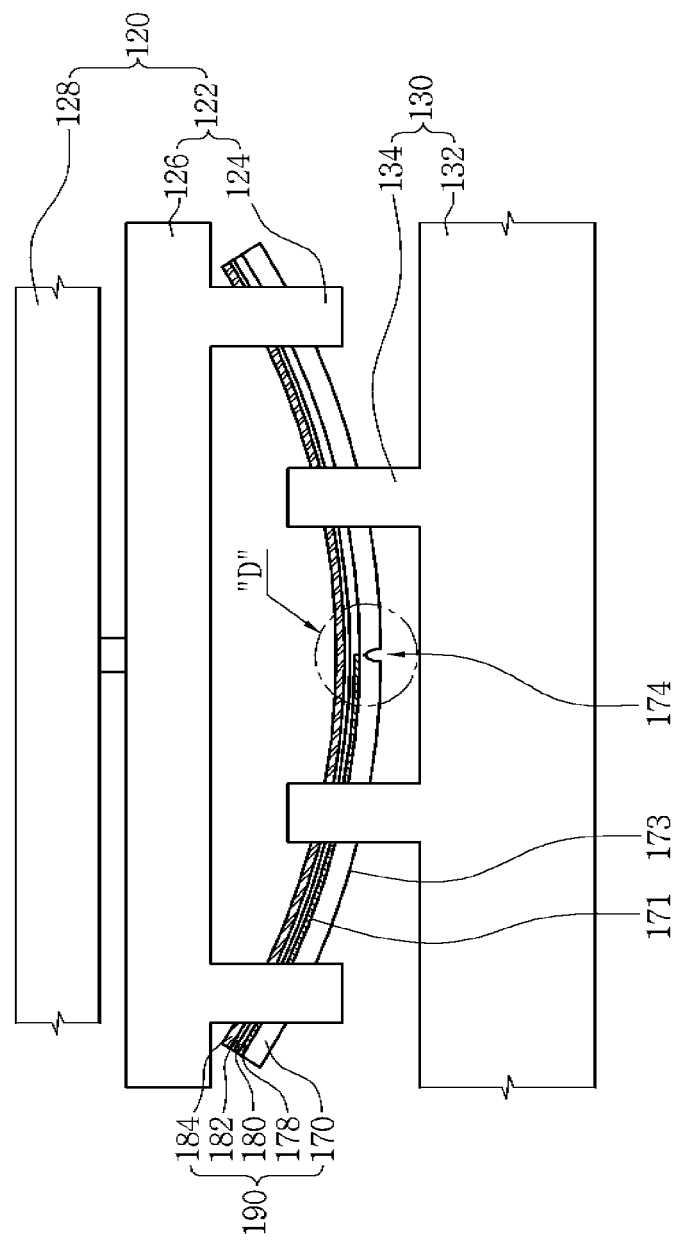
Figure 11:
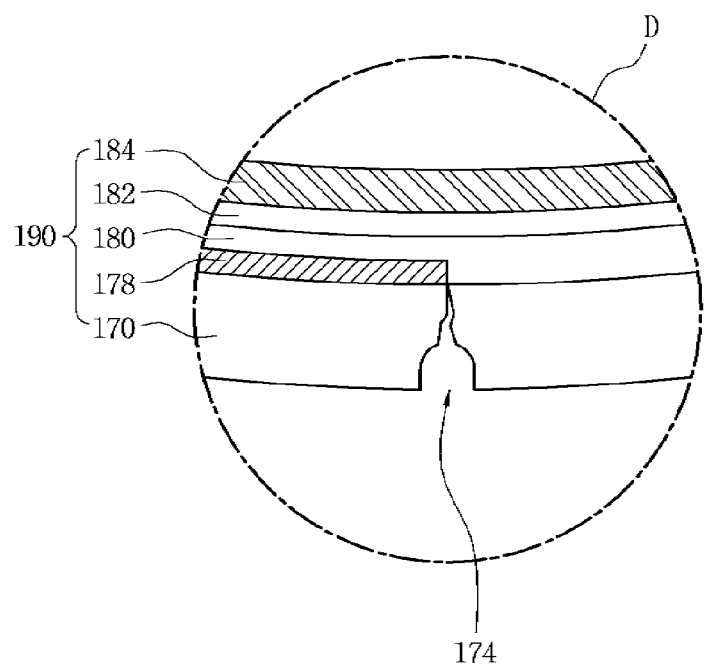

Referring to FIG. 10 and FIG. 11 illustrating a portion D of FIG. 10, when a pressure more than a damaging pressure of the substrate 170 is applied to the test sample 190 by the continuous movement of the actuator 130, a crack 194 may occur on the test sample 170. The crack 194 may occur on the notch 174 of the substrate 170, where the substrate 170 has the smallest thickness.

Figure 12:
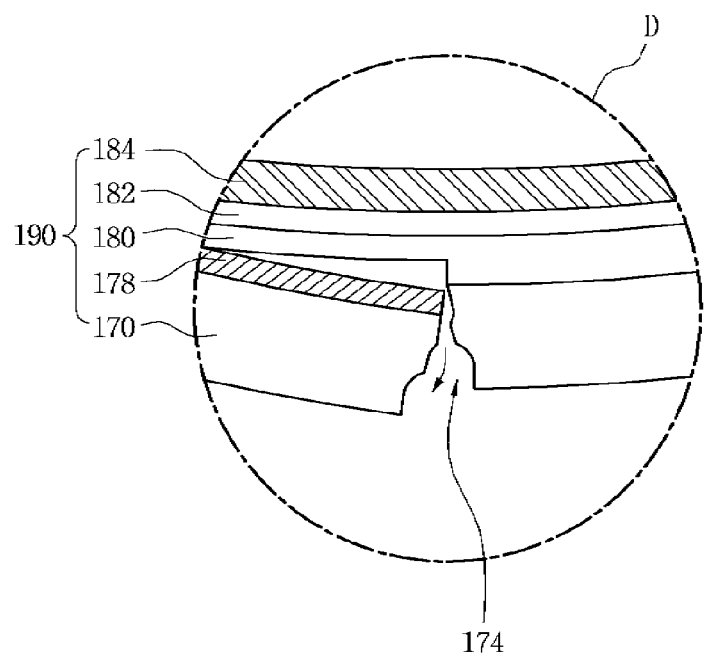
Figure 13:
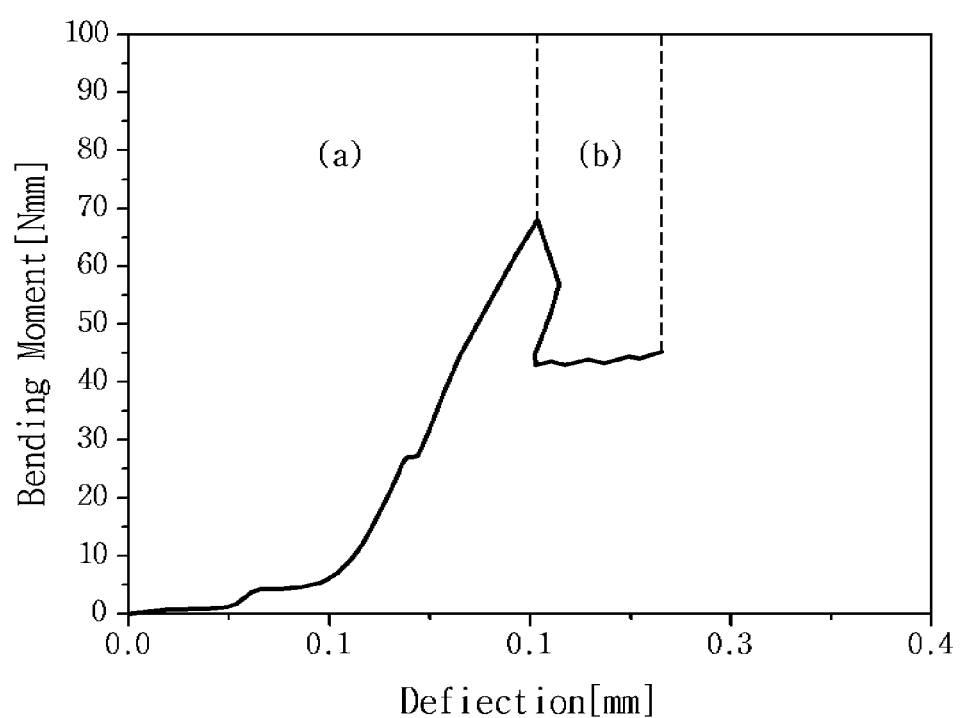
FIG. 13 is a diagram for explaining peel energy between thin films depending on pressure.

Referring to FIG. 12, a pressure more than interface adhesion energy between the first and second thin films 178 and 180 may be applied to the test sample 190 on which the crack has occurred. As a target which is to be peeled off in the adhesion test, the first thin film 178 can be peeled from the second thin film 180 by the pressure.

At this time, since the elastic plate 184 of the test sample 190 is formed of a metal including spring steel or a high molecular material having a larger elastic coefficient, the elastic plate 184 may be warped by the pressure, but may not be bent or damaged.

Referring to FIGS. 1 to 13, the pressure applied to the test sample 190 in the process of FIGS. 9 to 12 can be measured by the load cell 128 of the fixed part 120 provided in the adhesion test apparatus 100. The measured pressure data can be delivered to the computer 140.

The computer 140 may monitor the delivered pressure data to display changes in the pressure applied to the test sample. The pressure changes can be expressed in the form of a graph.

Specifically, an interval (A) of the graph may indicate pressures applied to the test sample 190 until the substrate 170 of the test sample 190 is damaged after a pressure is applied to the test sample 190.

A horizontal portion of an interval (B) of the graph may indicate a pressure at which the first thin film 178 is peeled from the second thin film 180 after the substrate of the test sample is damaged.

Therefore, the pressure value at the interval B may indicate the peel energy between the thin films, i.e., the adhesion between the thin films.

Considering the pressure at the time in which the first and second thin films 178 and 180 are peeled off, that is, the pressure at the interval B of the graph and the residual stress depending on the warpage of the test sample 190 calculated in FIG. 6, the computer 140 can derive the peel energy between the thin films. That is, the computer 140 can measure the adhesion between the thin films.

After that, although not shown, the actuator may be moved toward the fixed part to complete the adhesion test between the thin films according to exemplary embodiments.

The adhesion test method according to exemplary embodiments may be applied to a process of testing adhesion between a wafer and an adhesion member such as a die adhesive film (DAF) and an adhesive agent, as an elastic plate having large elasticity is used.

Further, the adhesion test method according to exemplary embodiments may be performed using a three-point bending apparatus.

In addition, the adhesion test method according to exemplary embodiments may be applied to adhesion test methods for various types of devices having thin films stacked therein, including display devices using semiconductor devices, thin film transistor-liquid crystal displays (TFT-LCDs), and organic light emitting diodes (OLEDs).

In exemplary embodiments, the elastic plate having such an elastic coefficient that it is warped but is not bent or damaged even by a large pressure may be used to form the adhesion test sample, and the four-point bending test apparatus may be used to perform the adhesion test.

Accordingly, when performing an adhesion test between the same kind or different kinds of thin films, it is possible to prevent damage such as a crack of the test sample. Therefore, the adhesion between the thin films can be accurately and stably measured.

Therefore, as the thin films are formed in an optimized shape to manufacture a semiconductor device, it is possible to improve the reliability of the semiconductor device.

The foregoing is illustrative of exemplary embodiments and is not to be construed as limiting thereof. Although a few exemplary embodiments have been described, those skilled in the art will readily appreciate that many modifications are possible in exemplary embodiments without materially departing from the novel teachings and advantages. Accordingly, all such modifications are intended to be included within the scope of this inventive concept as defined in the claims. In the claims, means-plus-function clauses are intended to cover the structures described herein as performing the recited function, and not only structural equivalents but also equivalent structures. Therefore, it is to be understood that the foregoing is illustrative of various exemplary embodiments and is not to be construed as limited to the specific embodiments disclosed, and that modifications to the disclosed embodiments, as well as other embodiments, are intended to be included within the scope of the appended claims.

What is claimed is:

1. A method of testing adhesion, comprising:
   forming thin films on a substrate;
   attaching an elastic plate to the substrate, wherein the elastic plate has a larger elastic coefficient than the substrate; and
   performing an adhesion test on the thin films using an adhesion test apparatus,
   wherein the performing the adhesion test includes applying pressure to the substrate and the elastic plate to peel the thin films from one another, and measuring energy when the thin films are peeled off, and
   wherein the pressure applied to the substrate is applied to both edges of the substrate toward the elastic plate, and the pressure applied to the elastic plate is applied to portions corresponding to positions between the pressure-applied portions of the substrate toward the substrate.

2. The method according to claim 1, wherein the thin films are formed on one surface of the substrate, and the elastic plate is attached to the one surface of the substrate through an adhesive member.

3. The method according to claim 2 further comprising, forming a notch across the other surface in the other surface of the substrate opposite to the one surface of the substrate.

4. The method according to claim 3, wherein at least one thin film, which is to be peeled off among the thin films, is formed such that one end thereof is disposed at a position vertically corresponding to the notch.

5. The method according to claim 1, wherein the thin films are formed of any one of an insulating layer, a metal layer, an adhesive agent, and an adhesive film.

6. The method according to claim 1, wherein a four point bending test apparatus is used as the adhesion test apparatus.

7. The method according to claim 1, wherein the substrate is formed of a semiconductor wafer, and the elastic plate is formed of a metal including spring steel or a high molecular material.

8. The method according to claim 1, further comprising, after attaching the substrate to the elastic plate, measuring the warpage of the elastic plate and the substrate attached to each other.

9. A method of testing adhesion, comprising:
   placing a test sample comprising a substrate and a plurality of thin films into a first set of supports and a second set of supports, the first set of supports being disposed on a fixed platform and the second set of supports being disposed on an actuator, the actuator facing the fixed platform;
   driving the actuator to move away from the fixed platform to warp the center part of the test sample toward the actuator; and
   measuring pressures applied to the test sample as the actuator moves away from the fixed platform until the plurality of thin films are peeled apart from one another; and
   determining the peel energy between the plurality of thin films,
   wherein the measuring pressures applied to the test sample includes applying pressure to the substrate and an elastic plate to peel the thin films apart from one another, and the determining the peel energy includes measuring energy when the thin films are peeled off, and
   wherein the pressure applied to the substrate is applied to both edges of the substrate toward the elastic plate, and the pressure applied to the elastic plate is applied to portions corresponding to positions between the pressure-applied portions of the substrate toward the substrate.

10. The method according to claim 9, further comprising before placing the test sample, attaching the elastic plate to the test sample,
    wherein the plurality of thin films are formed on one surface of the substrate, and the elastic plate is attached to the one surface of the substrate through an adhesive member with the thin films interposed therebetween.

11. The method according to claim 10, wherein determining the peel energy between the plurality of thin films comprises:
    calculating a pressure at a time in which the plurality of thin films are peeled off and a residual stress depending on warpage of the test sample.

12. The method according to claim 10, wherein warpage of the test sample occurs as the elastic plate and the substrate having different thermal expansion coefficients are attached to each other.

13. The method according to claim 10, further comprising, forming a notch across a surface of the substrate opposite to the one surface of the substrate.

14. The method according to claim 10, wherein the substrate is formed of a semiconductor wafer, and the elastic plate is formed of a metal including spring steel or a high molecular material.

15. A method of testing adhesion, comprising:
    forming a plurality of thin films on an upper surface of a substrate;
    attaching an elastic plate to an uppermost surface of the plurality of thin films, wherein the elastic plate is formed of a material having a larger elastic coefficient than the substrate; and
    determining a peel energy between the plurality of thin films,
    wherein the determining a peel energy comprises
        measuring pressures applied to the plurality of thin films as a test apparatus warps the plurality of thin films; and the peel energy is derived from the pressure applied at a time when the substrate is damaged and a residual stress based on the warpage of the combined elastic plate and substrate, wherein the measuring pressures applied to the thin films includes applying pressure to the substrate and the elastic plate to peel the thin films from one another, and measuring energy when the thin films are peeled off, and wherein the pressure applied to the substrate is applied to both edges of the substrate toward the elastic plate, and the pressure applied to the elastic plate is applied to portions corresponding to positions between the pressure-applied portions of the substrate toward the substrate.

16. The method according to claim 15, wherein the warpage of the combined elastic plate and substrate occurs as the elastic plate and the substrate having different thermal expansion coefficients are attached to each other.

17. The method according to claim 16, wherein the warpage of the combined elastic plate and substrate is measured by a shadow moiré system.

* * * * *